Figure 1:
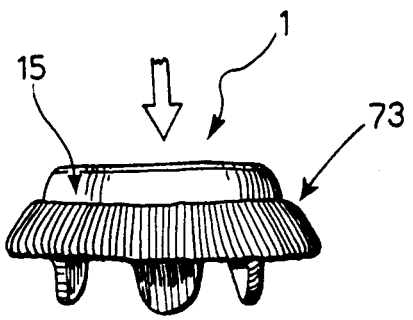

United States Patent [19]

Arru et al.

[11] Patent Number: 4,666,442
[45] Date of Patent: May 19, 1987

[54] CARDIAC VALVE PROSTHESIS WITH VALVE FLAPS OF BIOLOGICAL TISSUE

[75] Inventors: Piero Arru; Gioachino Bona, both of Turin; Maria Curcio, Saluggia; Franco Vallana, Turin, all of Italy

[73] Assignee: Sorin Biomedica S.p.A., Saluggia, Italy

[21] Appl. No.: 711,942

[22] Filed: Mar. 15, 1985

[30] Foreign Application Priority Data

Mar. 3, 1984 [IT] Italy .............................. 67249 A/84

[51] Int. Cl.$^4$ ................................................ A61F 2/24
[52] U.S. Cl. ....................................................... 623/2
[58] Field of Search ........................................ 623/2, 66

[56] References Cited

U.S. PATENT DOCUMENTS

| | | | |
|---|---|---|---|
| 4,084,268 | 4/1978 | Ionescu et al. | 623/2 |
| 4,149,277 | 4/1979 | Bokros | 623/66 |
| 4,172,295 | 10/1979 | Batten | 623/2 |
| 4,222,126 | 9/1980 | Boretos et al. | 623/2 |
| 4,275,469 | 6/1981 | Gabbay | 623/2 |
| 4,340,977 | 7/1982 | Brownlee et al. | 623/2 |
| 4,388,735 | 6/1983 | Ionescu et al. | 623/2 |
| 4,396,716 | 8/1983 | Marconi et al. | 623/2 X |
| 4,441,216 | 4/1984 | Ionescu et al. | 623/2 |
| 4,470,157 | 9/1984 | Love | 623/2 |
| 4,477,930 | 10/1984 | Totten et al. | 623/2 |
| 4,501,030 | 2/1985 | Lane | 623/2 |

*Primary Examiner*—Richard J. Apley
*Assistant Examiner*—Alan W. Cannon
*Attorney, Agent, or Firm*—Hedman, Gibson, Costigan & Hoare

[57] ABSTRACT

A cardiac valve prosthesis comprises an annular frame and a valve sleeve with a plurality of valve flaps which are forced apart by the blood passing through the prosthesis in one direction and which are mutually coapted by blood flow in the opposite direction. The frame of the prosthesis includes a rigid or semi-rigid stent constituted by a tubular body with a ring of apertures and with first and second end edges which, in the implanted position of the prosthesis, are respectively upstream and downstream with respect to the direction of flow of the blood through the prosthesis. Biocompatible textile completely covers the rigid stent: the covering has associated suture stitches some of which extend through the apertures of the said ring to attach the covering to the stent itself. The valve sleeve includes two sheets of biological tissue sutured together and wound into a tube, the radially outermost one having a shape which substantially reproduces the shape of the stent of the frame and the radially innermost one whereof, carrying the valve flaps, has a collar end portion which can be turned outwardly of the frame at the first end edge of the stent. The valve sleeve is fixed to the frame by further suture stitches, some of which extend through the apertures in the ends of the appendages of the frame stent. Other suture stitches connect the end edge of the collar end portion of the radially inner sheet to the covering of biocompatible textile.

9 Claims, 8 Drawing Figures

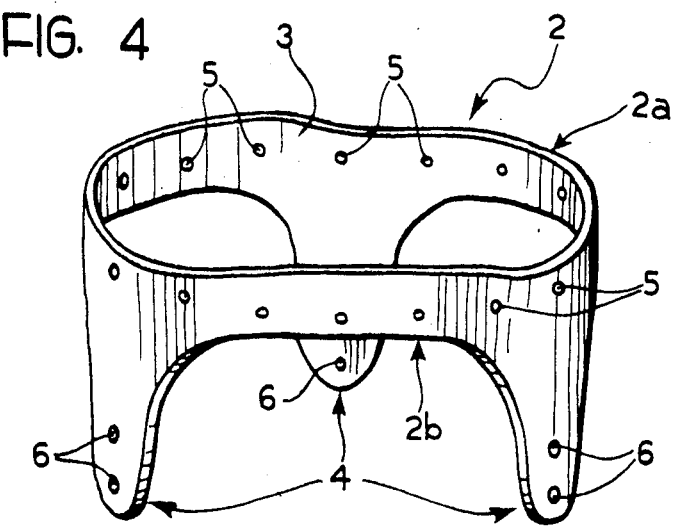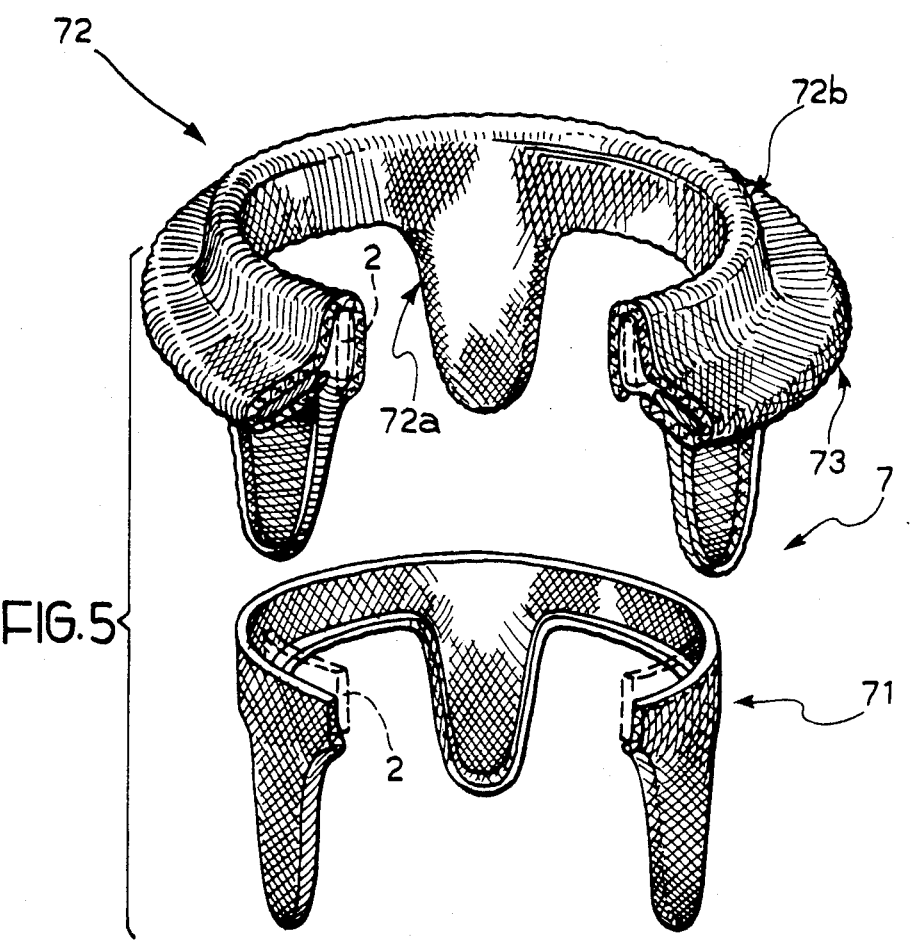

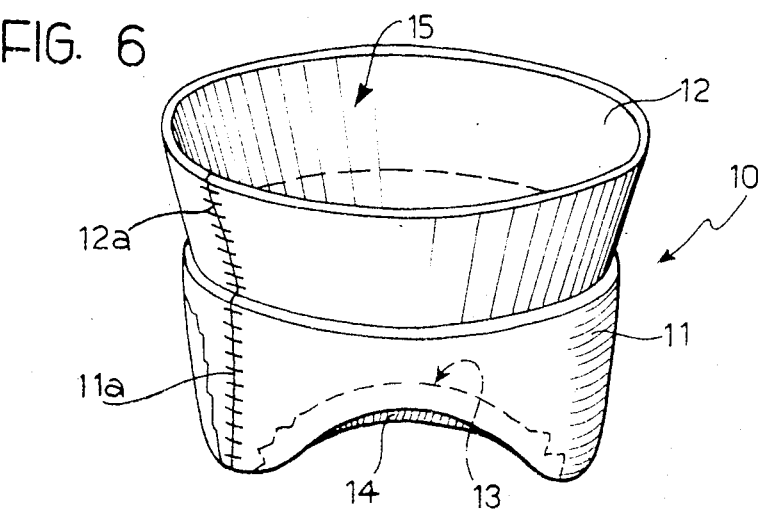
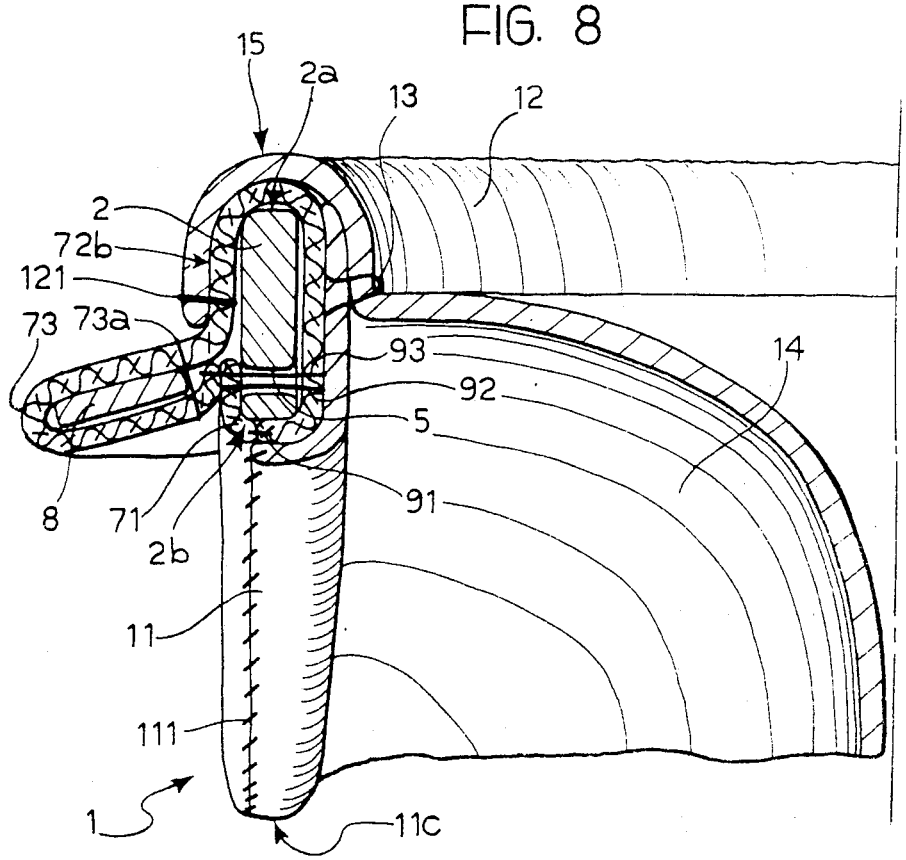

CARDIAC VALVE PROSTHESIS WITH VALVE FLAPS OF BIOLOGICAL TISSUE

DESCRIPTION

The present invention relates to cardiac valve prostheses having valve flaps of biological tissue. Cardiac valve prostheses of this type are generally used in clinical practice.

In particular, the present invention relates to a cardiac valve prosthesis comprising an annular frame through which blood can flow in the implant position of the prosthesis, and a valve sleeve of biological tissue with a plurality of valve flaps having free edges projecting inwardly of the frame and intended to be forced apart by the blood flow through the prosthesis in one direction and to prevent the blood flow in the opposite direction, being brought into a mutually mating position by the pressure exerted by the blood itself.

A prosthesis of this type is described, for example, in U.S. Pat. No. 4,084,268.

In comparison with cardiac prostheses including a rigid frame within which are mounted one or more shutters which pivot under the thrust of the blood flow, cardiac valve prostheses including valve flaps of biological tissue display a smaller thrombogenic activity and reproduce more faithfully the fluid flow process which characterises the operation of natural cardiac valves.

The biological tissue is normally constituted by animal pericardial tissue, preferably taken from cattle or pigs. It has also been proposed to use tissue comprising fascia lata or layers of dura mater of heterologous, homologous or autologous origin.

When obtained, the tissue intended to be used for the manufacture of valve flaps is subjected to cleaning and to a selection process so that only the structurally more uniform parts are kept.

The biological tissue is subsequently subjected to a treatment, so-called "fixation", by immersion in solutions of glutaraldehyde of controlled pH, possibly enriched with anti-calcifying additives. The "fixation" treatment (or "stabilisation" according to another term used in the art) is intended to facilitate the establishment of cross links between the various forms of glutaraldehyde and the amine groups in the proteins constituting the collagen of the tissue.

The object of the present invention is to provide a cardiac valve prosthesis of the type specified above which has improved chracteristics compared with the already known prostheses and which allow the prosthesis itself to operate regularly and reliably for very long implant periods, minimising the possibilities of formation of blood clots and thromboembolisms in the blood flow.

According to the present invention, this object is achieved by virtue of a cardiac valve prosthesis of the type specified above, characterised by the following, in combination:

(a) the frame of the prosthesis has a rigid or semi-rigid stent and a covering of biocompatible textile wherein the stent has a tubular body the wall of which has a ring of apertures and which has first and second end edges which, in the implanted position of the prosthesis, are upstream and downwstream respectively with respect to the direction of free flow of the blood through the prosthesis; the tubular body also having integral appendages which project from the second end edge in an axial direction relative to the tubular body itself and each of which has respective apertures located adjacent its free end, and (b) the covering of biocompatible textile is wrapped completely over the rigid or semi-rigid stent; the covering having associated first suture stitches some of which extend through the apertures in the said ring to attach the covering to the stent itself, (c) the valve sleeve includes two sheets of biological tissue sutured together by second suture stitches and wound into a tube, of which the radially outermost one has a shape which substantially reproduces the shape of the said stent and the radially innermost one, carrying the said valve flaps, has an end collar portion turned outwardly of the frame in correspondence with the first end edge of the stent of the frame itself; the valve sleeve having associated third suture stitches for fixing it to the frame extending through the end apertures in the appendages of the stent and fourth suture stitches connecting the end edge of the end collar portion of the radially innermost sheet to the covering of biocompatible textile, and (d) the radially outer sheet of the valve sheet has associated fifth suture stitches connecting the radially outer sheet to the covering of biocompatible textile adjacent the said second end edge of the stent and is connected to the frame of the prosthesis solely by means of these fifth suture stitches and the third suture stitches extending through the end apertures in the appendages of the stent itself.

By virtue of these characteristics, a valve prosthesis is provided which has considerable advantages in terms of operation, reliability and lifetime over prostheses provided with valve flaps of known type.

In the first place there is a reduction in the mechanical forces to which the biological tissues of the prosthesis, particularly the valve flaps, are subject. The sheet (thin sheet) of biological tissue which is radially innermost and which carries the valve flaps, is in fact connected to the stent of the frame only in an indirect manner through the covering textile or radially outermost sheet of the sleeve. The mechanical forces to which the valve flaps are subject during operation of the prosthesis according to the invention are thus significantly smaller than the forces to which the flaps themselves would be subject if directly connected to a rigid structure such as that of the stent of the prosthesis frame.

In the second place, all the parts of the prosthesis intended to come into direct contact, in use, with the blood flow are covered by the biological tissue. The inner wall of the frame is in fact covered by the radially outermost sheet of the valve sleeve which substantially reproduces its shape, as well as by the covering of biocompatible textile. The end edge (upstream edge) of the prosthesis upon which the blood flow which passes freely through the prosthesis will impinge is then completely covered by the end portion of the radially inner sheet of the valve sleeve turned outwardly of the frame in the form of a collar.

According to a preferred embodiment, the rigid or semi-rigid stent has integral appendages distributed substantially uniformly around the periphery of the tubular body and the tubular body has an axial extent which varies angularly with mininum values in correspondence with the regions between two adjacent appendages.

This particular configuration of the stent of the frame is intended to minimise the area of the inner surface of the frame against which the valve flaps may be thrust relatively vigorously during their opening apart under the action of the blood flow.

Further developments of the invention, outlined in the claims, significantly facilitate the assembly of the prosthesis.

A particularly relevant factor of a second preferred embodiment of the prosthesis according to the invention is that the covering of biocompatible textile which covers the stent of the frame is at least partially coated with biocompatible carbonaceous material applied by cathode sputtering using a target constituted essentially of carbon. The first, second, third, fourth and fifth suture stitches are also preferably constituted at least partly by thread covered with biocompatible carbonaceous material.

Figure 2:
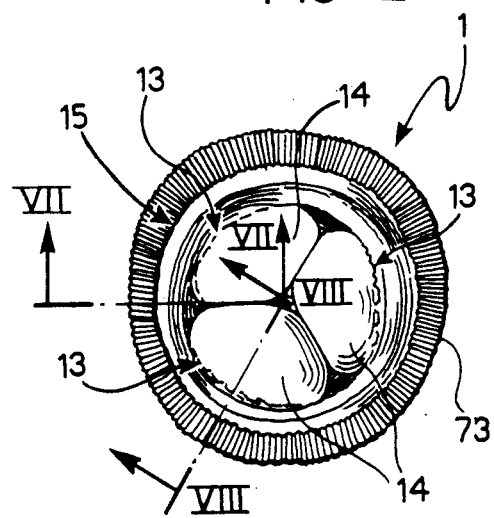
Figure 3:
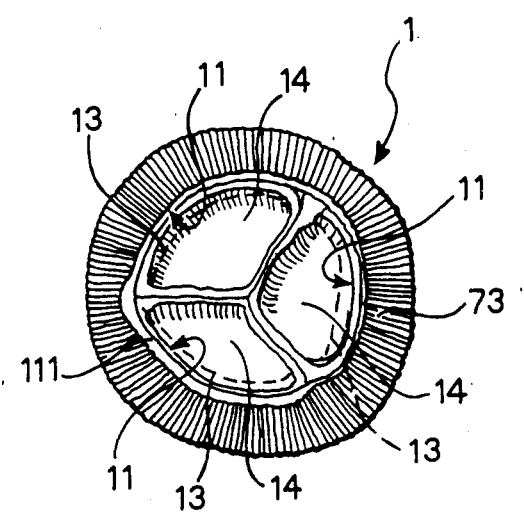
Figure 7:
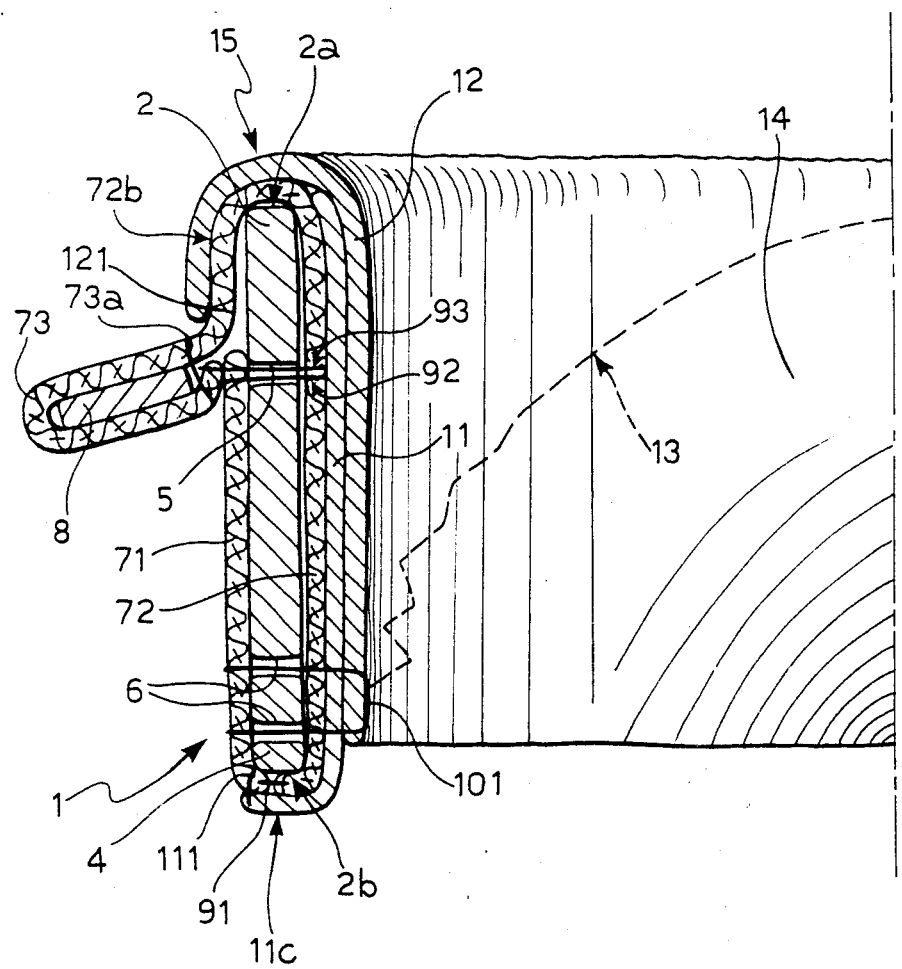

The invention will now be described, purely by way of non-limiting example, with reference to the appended drawings, in which:

FIG. 1 is a perspective view of the whole of a cardiac valve prosthesis formed according to the invention, FIG. 2 and FIG. 3 are respectively opposite axial end views of the valve prosthesis of FIG. 1, FIGS. 4 to 6 are perspective views (exploded in the case of FIG. 5) illustrating several of the elements of the prosthesis of FIGS. 1 to 3 in isolation, FIG. 7 is a section taken on the line VII—VII of FIG. 2, and FIG. 8 is a view taken on the line VIII—VIII of FIG. 2.

In the drawings, a cardiac valve prosthesis intended for implantation in the cardiac wall to replace a natural valve is generally indicated 1.

In the implant position, the prosthesis is sutured to the cardiac wall in the zone surrounding the orifice formed by the removal of the autologous valve flaps.

By way of summary, the prosthesis is constituted by a support structure (frame) of generally annular form which is intended to be sutured to the cardiac wall and which houses within it a valve sleeve including valve flaps of biological tissue. As generally known to the expert in the art and as will be better explained below, the prosthesis is intended to be traversed by the blood flow in the direction schematically indicated by the arrow in FIG. 1 and to prevent the flow of blood in the opposite direction.

The frame of the prosthesis includes a rigid or semi-rigid stent 2 illustrated separately in FIG. 4.

The stent 2 is constituted essentially by a tubular body 3 of small axial extent from which a trio of elongate appendages 4 project, these being equiangularly distributed around the periphery of the tubular body.

The stent 2 thus has two end edges indicated 2a and 2b respectively which in the implant position of the prosthesis are respectively upstream and downstream with respect to the direction of the free flow of blood through the prosthesis (arrow in FIG. 1).

The upstream end edge 2a is substantially circular or undulate as illustrated in FIG. 4, with recessed zones located in correspondence with the appendages 4. The downstream end edge 2b, however, follows the profile of the appendages 4 and is thus ideally divided into three arcuate portions each of which extends from the top of one of the appendages 4 to the top of an adjacent appendage 4.

By virtue of the generally arcuate profile of each of the sections of the edge 2b the axial dimension of the tubular portion 3 of the stent 2 in the central region between two adjacent appendages 4 has a minimum value for the purposes which will be better explained below.

The stent 2 is constituted by a single piece of biocompatible material such as, for example titanium, chromium-cobalt alloys or cobalt based alloys, or even the plastics materials known by the trade names "TEFLON" or "DELRIN". When the stent 2 is made from plastics material an annular metal insert is normally embedded therein to allow the prosthesis to be located radiologically after implant in the patient.

The wall of the stent 2 has apertures some of which are generally indicated 5 form a ring, these apertures 5 which opening into the tubular portion 3 of the stent 2 in a generally circular path lying in a plane parallel to the general plane of the end edge 2a. Alternatively the apertures 5 may be arranged along a path which follows the undulate profile of the edge 2a (see FIG. 4).

Other apertures indicated 6, however, pass through the appendages 4 near their free ends. In particular, each appendage 4 has a pair of apertures 6 aligned longitudinally relative to the appendage itself.

A covering of biocompatible textile, for example the textile known by the trade name "Dacron Fabric" is generally indicated 7 and wraps the stent 2 entirely.

The structure of the covering 7, which is a type of stocking or knitting which covers the frame 2, is illustrated in detail in FIG. 5.

The covering 7 is constituted essentially by two shaped sheets of biocompatible Dacron fabric indicated 71 and 72 respectively.

The first sheet 71 is intended to be applied to the outer surface of the stent 2 so as to cover the portion of this surface approximately between the ring of apertures 5 and the end edge 2b.

The sheet 71, normally made from a tubular knitted Dacron thus has a general shape which reproduces the shape of the outer surface of the stent 2 save only for its smaller axial extent.

The sheet 72, also made from a knitted Dacron and illustrated with a part removed for greater clarity in FIG. 5, has instead an axial extent which is much greater than that of the stent 2. It thus includes a so-called lower portion 72a the shape of which reproduces approximately the shape of the inner surface of the stent 2, and an upper end portion generally indicated 72b which can be turned over in the form of a collar outwardly of the frame 2.

The portion 72b of the sheet 72 forms a wide annular loop 73 on the outer face of the stent 2, defining a ring for the suturing of the prosthesis to the cardiac tissues.

Within the loop 73 is an annular cushion 8 of biocompatible material which forms a stiffening core for the suture ring of the prosthesis. The cushion 8 is constituted by a ring of textile through which the surgical thread used for the suturing of the prosthesis to the cardiac tissue can easily be passed.

The covering 7 is closed by the connection of the sheet 71 and 72 and fixed to the stent 2 by suture stitches 91, 92, and 93.

These stitches are clearly visible only in the sections of FIGS. 7 and 8.

In particular, the suture stitches 91 connect the sheet 71 and the sheet 72 along respective facing edges along the downstream edge 2b of the stent 2.

The stitches indicated 92, however, extend through the apertures 5 connecting the regions of the sheet 71 and the sheet 72 which face each other at the opposite ends of these apertures.

The stitches indicated 93 also extend through the apertures 5 connecting the regions of the sheets 71 and 72 facing each other at the two ends of the apertures 5. The suture stitches 93 extend further outwardly of the frame of the prosthesis, being connected to the upper edge of the sheet 71, that is to say the edge of the sheet 71 facing the apertures 5, the end edge of the portion 72b of the sheet 72 forming the loop 73. The stitches 93 are connected to the end edge of the loop 73 to which further stitches 73a are connected which close the loop 73 around the cushion 8.

In the claims which follow, the suture stitches 73a, 91, 92 and 93 are generally identified as "first suture stitches".

The assembly formed by the stent 2 covered by the biocompatible covering 7 constitutes the supporting structure or frame of the prosthesis for receiving within it the sheets of biological material defining the valve flaps.

Preferably the covering textile 7 and the thread used for the suture stitches 73a, 91, 92 and 93 is coated (before or possibly even after assembly on the stent 2) with a coating of biocompatible carbonaceous material.

This coating serves the function of at least partially inibiting reactions which are at the root of throbogenic processes and the uncontrolled growth of natural tissues around the prosthesis 1.

Indeed, although a small growth of natural tissue in the region in which the suture ring 73, 8 is applied to the cardiac wall is considered beneficial for the better anchoring of the prosthesis, anomolous growth of tissue in the region inside the frame could alter the blood flow conditions through the prosthesis, causing a deterioration in its operating characteristics until it is necessary to replace it.

Consequently, although it is possible to apply it over the whole surface of the textile 5, the carbonaceous coating is preferably applied while leaving uncovered, for example, a portion of suture ring over which the blood will not flow in the implanted position of the prosthesis.

Thus the growth of natural tissues is allowed in the zones in which this growth is beneficial and on the other hand is opposed where this phenomenon would have harmful effects with regard to the operational efficiency of the prosthesis.

The coating of biocompatible carbonaceous material is applied by cathode sputtering with the use of a target constituted by a carbonaceous material selected from the group consisting of graphite, glassy carbon and carbon with a turbostratic structure.

The application of a carbon-based biocompatible material by cathode sputtering is described in detail in the European Patent Application published under the number 0102328 in the name of the same applicants. The application of the coating by cathode sputtering may be carried out at temperatures close to the ambient temperature, thus avoiding damage to the textile 7 or to the stent material 2, when the coating is applied to the textile after its fixing to the stent 2.

Within the axial orifice of the frame of the prosthesis is a valve sleeve 10 the structure of which is illustrated in detail in FIG. 6.

The sleeve 10 is constituted by two sheets 11, 12 of inert biological material. Biological tissues constituted by cattle or pig pericardial tissues may be used successfully for the manufacture of the sleeve 10 although the use of biological tissues of different types and origins is not excluded. For example it has been proposed to use a membrane of cranial or cervical dura mater or even membranes of fascia lata taken from man or animals as the biological tissue.

After removal, the biological tissue is subjected to a cleaning operation. Subsequently it is subjected to a selection so as to keep only those parts which are structurally most homogeneous and suitable.

The sheets of biological tissue selected are then subjected to a treatment for stabilising their elastic properties and mechanical strength and to give them characteristics of chemical inertness to blood.

This operation, generally known as "fixation" or "stabilisation" is normally carried out by the immersion of the tissue in solutions of glutaraldehyde having a controlled pH, possibly enriched with anti-calcifying additives. The fixation operation in general results in the formation of stable cross links between the various forms of the glutaraldehyde and the amine groups of proteins constituting the cologen of the tissue.

The treatment times may vary widely in accordance with the characteristics of the biological tissue subjected to fixation and the manner in which the fixation is carried out. During the treatment, the concentration of the fixation solution is varied. For example, when glutaraldehyde solutions are used, after an initial, so-called prefixation stage, carried out with a 0.2% solution of glutaraldehyde, the solution is changed to concentrations of the order of 0.5% for the final fixation stage.

The biological tissue may be fixed finally before it is cut and shaped for the sheets constituting the sleeve 10. However it is also possible to use non-fixed biological tissue, or tissue subjected solely to the initial stage in the fixation process for the manufacture of the sleeve 10, particularly with regard to the sheet 12. In particular it is possible to shape the sheet 12 by using a pressure gradient generated in the fixation liquid for this purpose.

A method and apparatus for the shaping and simultaneous final fixing of biological tissue for use in the manufacture of valve flaps for a cardiac prosthesis is described in European Patent Application published under the number 0133420 in the name of the same applicants, the specification of which is incorporated herein as a reference.

For an understanding of the present invention it will suffice to note that the valve sleeve 10 is constituted essentially by two shaped sheets of biological tissue 11, 12 closed into a tube by suture stitches 11a 12a along opposing end edges of the two sheets. Consequently, the two sheets closed into a tube are at least partly fitted one within the other. For this reason, in the description below and in the claims which follow, the two sheets 11 and 12 are identified generally as the radially outermost sheet and the radially innermost sheet respectively. The radially outermost sheet 11 constitutes essentially a support band for the fixing of the sleeve 10 to the frame of the prosthesis.

It thus has a shape substantially identical to that of the internal face of the stent 2 covered by the covering 7.

In the assembled position of the prosthesis the outer sheet 11 of the sleeve 10 is fixed to the inner sheet 72 of the covering 7 by suture stitches 111 stitched through the end edge of the sheet 72 (72a) extending so as to cover the edge 2b of the stent 2 and the margin 11c of the sheet 11 facing it.

The suture stitches 111 are preferably located along the margin 11c of the sheet 11 which faces slightly outwardly of the frame. This is in order to avoid the inner sheet 12 of the sleeve coming into contact with the stitched region itself during operation of the prosthesis, with risk of wear. The arrangement described means that during operation the surface of the inner sheet 12 of biological material comes into contact solely with a similar material, minimising abrasion due to friction.

The inner sheet 12 of the sleeve is fixed to the outer sheet 11 by suture stitches 13 made with surgical thread possibly covered by a coating of biocompatible carbonaceous material substantially similar to that described previously with reference to the textile 7 and to the suture stitches 73a, 91, 92 and 93. The suture stitches 13 (second suture stitches) extend along half moon-shaped paths. Each suture line defines a respective half moon edge of one of the three valve flaps 14 of the prosthesis according to the invention. Preferably (see FIGS. 6 and 7), the stitches 13 are "straight" stitches co-extensive with the half moon path in the central part of the path itself and having a zig-zag course at the ends of this path.

The valve flaps 14 have a generally bow-shaped configuration with their concavity facing outwardly of the valve sleeve 10.

The manner in which the valve flaps 14 are given the said bow-shaped configuration is described in European Patent Application No. 0133420 in the name of the same applicants and mentioned above. For the same purpose, but with less satisfactory results, other processes known to the expert in the art may be used.

Under rest conditions, the valve flaps 14 converge inwardly of the sleeve 10, being disposed in an edge mating position in the stellar configuration seen in FIGS. 2 and 3 in which the convex faces and the concave faces of the flaps 14 are visible respectively.

The sheet 12 also has a flared end collar portion 15 which projects axially beyond the outer sheet 11. The collar portion 15 is turned outwardly of the frame of the prosthesis as is most clearly seen in FIGS. 1, 2, 7 and 8 and is retained in the final assembled position by suture stitches 121 which connect the end edge of the portion 15 itself to the second sheet of the covering of biocompatible textile 72 in correspondence with the radially inner edge of the upper face of the loop 73.

The function of the collar portion 15 is to ensure that the end edge of the prosthesis upon which the blood flow impinges is completely covered by biological tissue with its anti-thrombogenic properties.

The radially innermost sheet 12 of the sleeve 10 is also fixed to the outer sheet 11 in correspondence with apex parts of the appendages 4 of the stent 2 by further suture stitches 101 (FIG. 7) each having a generally U-shape.

In particular, starting from a first end located outside the sheet 71 of the covering textile, the thread of each stitch 101 penetrates one of the apertures 6 and passes successively through the inner sheet 72 of the covering textile, the outer sheet 11 and the inner sheet 12 of the sleeve. On the inner surface of the latter sheet 12, the thread forms a loop, from which the thread itself passes again this time in reverse order, through the inner sheet 12 and the outer sheet 11 of the sleeve 10 and the inner sheet 72 of the covering 7 and then passes through the other aperture 6 and the outer sheet 71 of the biocompatible textile covering and emerges outside the prosthesis at another end. The configuration of the stitch 101 described has been shown to be particularly advantageous both in terms of ease of formation and in terms of functional efficiency, reliability and structural strength. In particular, in the region of application of each stitch 101, the wall of the inner sheet 12 is laid on the wall of the underlying outer sheet 11 without giving rise to bends or folds which, in operation of the prosthesis, could act as starting points of ruptures or perforations in the biological tissue.

The suture stitches 101, and also the suture stitches 111 and 121, may be made with a thread having a coating of biocompatible carbonaceous material similar to that covering the stitching 73a, 91, 92, 93 and 13 previously described.

With reference by way of example to an atrioventricular implant, in the diastolic phase, the blood which flows out of the atrium enters the ventricle by passing through the prosthesis in the direction indicated schematically by the arrow in FIG. 1. In this direction of flow, the blood impinges on the convex faces of the valve flaps 14, forcing their free edges apart and forming a central substantially cylindrical aperture in the body of the prosthesis through which the blood itself can flow freely. This aperture is defined in practice by the inner sheet 12 of the valve sleeve 10. In particular, the manner of application of the stitches 101 described previously ensures that there are no restrictions in the flow section for the blood at the outlet end of the prosthesis.

Immediately a pressure difference is established through the prosthesis as a result of the contraction of the ventricle inducing a flow of blood in the opposite direction, the pressure exerted by the blood itself on the concave faces of the valve flaps 14 forces the free edges of these flaps into the mating position illustrated in FIGS. 2 and 3. Under these conditions blood flow through the prosthesis is prevented.

When the pressure gradient across the prosthesis again reverses as a result of the cardiac activity, the free edges of the flaps 14 again diverge, allowing the free flow of blood. In some situations of operation the force exerted by the blood flow in opening the flaps 14 may be very strong and cause the flaps to be projected rather violently against the inner surface of the frame. In the prosthesis according to the invention the harmful effect of this phenomenon is limited by virtue of the particular shaping of the stent 2 and the markedly reduced axial extent of the tubular portion 3 of the stent 2 in the central region between the adjacent appendages 4. Thus in fact the extent of the frame portion against which the base region of the flaps 14 may accidentally be projected is reduced to a minimum.

Naturally the principle of the invention remaining the same, constructional details and embodiments may be varied widely with respect to those described and illustrated without thereby departing from the scope of the present invention.

We claim:

1. A cardiac valve prosthesis which includes valve flaps of biological tissue and which operates regularly and reliably for long implant periods while minimizing the possibilities of formation of blood clots and thromboembolisms in the flow of blood, comprising:

an annular frame through which blood can flow in the implant of the prosthesis, including a stent with a tubular body the wall of which has a ring of first apertures and which has first and second end edges which, in the implanted position of the prosthesis, are respectively upstream and downstream relative to the direction of free flow of the blood through the prosthesis, said tubular body also having integral appendages which project from said second edge in an axial direction relative to the tubular body and each of which has respective second apertures located adjacent its free end, and a covering of biocompatible textile wrapped completely over the stent, the covering having associated therewith first suture stitches at least some of which extend through said first ring of apertures to attach said covering to said stent;

a valve sleeve of biological tissue including a radially outer sheet and a radially inner sheet of biological tissue formed into a tube and connected together by second suture stitches, wherein said radially outer tubular sheet has a shape which substantially reproduces the shape of said stent and is insertable thereinto, and wherein said radially inner tubular sheet has an end collar portion with an edge portion turned outwardly of said frame in correspondence with said first edge of said stent, and a plurality of valve flaps with free edges projecting inwardly of said frame and intended to be forced apart by the blood flow through the prosthesis in one direction and to prevent the blood flow in the opposite direction, said free edges being brought into mutually mating position by the pressure exerted in the blood itself; and third suture stitches extending through said second apertures in said appendages of said stent and connecting said outer sleeve to said frame, fourth suture stitches connecting said outer end of said collar portion to the covering of said adjacent biocompatible textile, and fifth suture stitches connecting said radially outer sheet to the covering of the biocompatible textile adjacent said second edge of said stent wherein said fifth suture stitches are the sole means for connecting said radially outer sheet to said frame.

2. The cardiac valve prosthesis of claim 1, wherein the integral appendages of the stent are distributed substantially uniformly around the periphery of the tubular body of the stent itself and wherein said body has an axial extent which varies angularly, with mimimum values corresponding with the regions between adjacent said appendages.

3. The cardiac valve prosthesis of claim 1, wherein the covering of biocompatible textile includes a first sheet applied to the outer surface of the stent in the region between said ring of first apertures and the second end edge, and a second sheet applied to the inner surface of the stent and having an end portion which extends outwardly of the stent and forms a loop in correspondence with said ring of first apertures and provides an outer annulus for suturing the prosthesis to the cardiac wall, said end portion having an end edge; the first suture stitches further including a first group of stitches connecting the first and the second sheets of biocompatible textile together at their mutually facing edges along the said second end edge of the stent, and a second and a third group of stitches extending through said first apertures and connecting the region of the second sheet of the covering facing the ring of first apertures respectively to the region of the first sheet of biocompatible textile facing said first apertures and to the end edge of said end portion of the second sheet forming said loop through said region of said first sheet.

4. The cardiac valve prosthesis of claim 3, wherein said end edge of said end collar portion of the radially inner sheet of biological tissue extends into at least marginal contact with the upper face of said loop.

5. The cardiac valve prosthesis of claim 1, wherein the radially outer sheet of the valve sleeve has a margin partially turned over the covering of biocompatible textile in correspondence with the second end edge of said stent and wherein the fifth suture stitches are formed along the partially turned margin.

6. The cardiac valve prosthesis of claim 1, wherein in the region of application of each of said third suture stitches the radially inner tubular sheet of the valve sleeve rests on the radially outer tubular sheet of said valve sleeve.

7. The cardiac valve prosthesis of claim 1, wherein the covering of biocompatible textile is at least partially coated with biocompatible carbonaceous material.

8. The cardiac valve prosthesis of claim 7, wherein the first, second, third, fourth and fifth suture stitches are at least partly constituted by thread coated with biocompatible carbonaceous material.

9. The cardiac valve prosthesis of claim 7, wherein the biocompatible carbonaceous material is applied by cathode sputtering with the use of a target constituted essentially of carbon.

* * * * *

UNITED STATES PATENT AND TRADEMARK OFFICE
CERTIFICATE OF CORRECTION

PATENT NO. : 4,666,442

DATED : May 19, 1987

INVENTOR(S) : ARRU ET AL

It is certified that error appears in the above—identified patent and that said Letters Patent is hereby corrected as shown below:

The priority of the application should read:

Change "March 3, 1984" to--March 16, 1984--.

Signed and Sealed this

Twenty-second Day of December, 1987

Attest:

DONALD J. QUIGG

Attesting Officer      Commissioner of Patents and Trademarks